United States Patent
Ohtsuka et al.

(10) Patent No.: US 6,391,597 B1
(45) Date of Patent: May 21, 2002

(54) METHOD FOR PRODUCING OPTICALLY ACTIVE 1-(4-T-BUTYLPHENYL)-5-OXO-3-PYRROLIDINE CARBOXYLIC ACID AND/OR AN ENANTIOMERIC ESTER THEREOF

(75) Inventors: Koutaro Ohtsuka; Shunji Kamiyama; Masafumi Moriwaki, all of Kobe (JP)

(73) Assignees: Nagase & Company, Ltd., Osaka; Taiho Pharmaceutical Co., Ltd., Tokyo, both of (JP)

( * ) Notice: Subject to any disclaimer, the term of this patent is extended or adjusted under 35 U.S.C. 154(b) by 0 days.

(21) Appl. No.: 09/557,131

(22) Filed: Apr. 25, 2000

(51) Int. Cl.[7] .............................. C12P 17/10; C12P 1/04; C12N 1/20
(52) U.S. Cl. .................... 435/121; 435/252.5; 435/170; 435/833
(58) Field of Search .................................. 435/121, 833

(56) References Cited

U.S. PATENT DOCUMENTS 5,106,736 A * 4/1992 Patel et al. ................. 435/106

FOREIGN PATENT DOCUMENTS

| JP | 3-275666 | | 12/1991 |
| JP | 6-192221 | | 7/1994 |
| JP | 10248561 | * | 9/1998 |
| JP | 11-113594 | | 4/1999 |

* cited by examiner

*Primary Examiner*—Irene Marx
*Assistant Examiner*—Vera Afremova
(74) *Attorney, Agent, or Firm*—Renner, Otto, Boisselle & Sklar, LLP

(57) ABSTRACT

A method for producing an optically active 1-(4-t-butylphenyl)-5-oxo-3-pyrrolidine carboxylic acid and/or an enantiomeric ester thereof which includes treating an ester of (±)-1-(4-t-butylphenyl)-5-oxo-3-pyrrolidine carboxylic acid with an esterase derived from *Bacillus brevis* 042-24 (FERM BP-5872).

5 Claims, No Drawings

METHOD FOR PRODUCING OPTICALLY ACTIVE 1-(4-T-BUTYLPHENYL)-5-OXO-3-PYRROLIDINE CARBOXYLIC ACID AND/OR AN ENANTIOMERIC ESTER THEREOF

BACKGROUND OF THE INVENTION

1. Field of the Invention

The present invention relates to a method for producing optically active 1(4-t-butylphenyl)-5-oxo-3-pyrrolidine carboxylic acid (hereinafter, referred to as TBPA) and/or an enantiomeric ester thereof.

2. Description of the Related Art

The TBPA is useful as an intermediate for producing an optically active compound expressed by general formula (1):

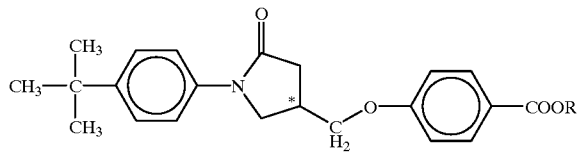

(1)

where R represents a hydrogen atom or a lower alkyl group, and * represents an asymmetric carbon atom. The compound expressed by general formula (1) inhibits fatty acid synthesis and cholesterol synthesis, and is useful as an agent for treating hyperlipemia. Hereinafter, the compound expressed by general formula (1) is referred to as Compound (1).

Conventionally, a large number of compounds having pharmacological activities have been used in the form of a mixture of optical isomers. However, in many cases, only one of the optical isomers has desirable activities. Further, it is known that the other isomer, which is unnecessary, may be toxic. Therefore, there is a great demand for a stereochemically pure compound for the purpose of providing effective and safe medicines.

Regarding Compound (1), Japanese Laid-Open Patent Publication No 3-275666 discloses the use of Compound (1) as an agent for treating hyperlipemia because it is effective in inhibition of fatty acid synthesis and cholesterol synthesis. Following this disclosure, it is desired to provide a practical and industrial method for producing an optically active intermediate for producing Compound (1).

The aforementioned Japanese Laid-Open Patent Publication No. 3-275666 describes the racemic and optically active compounds expressed by general formula (1). However, although this publication provides a general description of a method for producing either one of the optically active compounds, it does not specifically disclose any method that can be used practically as an industrial method.

On the other hand, Japanese Laid-Open Patent Publication No. 6-192221 discloses a method for producing an optically active TBPA which is an intermediate of Compound (1). According to this method, an optically active TBPA and an enantiomeric ester thereof are produced by treating an ester of (±) TBPA with a hydrolytic enzyme derived from *Aspergillus oryzae* or *Trichoderma harzianum*. This publication also discloses a method for obtaining Compound (1), using TBPA produced by the above method as a raw material.

In the enzymatic production of such an organic compound as described above, it is preferable that a starting material should be dissolved in an organic solvent of various types at a high concentration and reacted at relatively high temperature in order to ensure a high reaction efficiency. Since an enzyme derived from *Aspergillus oryzae* or *Trichoderma harzianum* is unstable with respect to organic solvents and heat, its activity deteriorates significantly during the reaction. For this reason, a large amount of enzyme is required for the reaction and the other conditions for the reaction are also restricted. Therefore, a method using such an enzyme is not preferable as an industrial method.

SUMMARY OF THE INVENTION

Therefore, with the foregoing in mind, it is an object of the present invention to provide a method for efficiently producing TBPA having a high optical purity by utilizing an enzyme having high substrate specificity and optical selectivity.

The present invention provides a method for producing an optically active TBPA and/or an enantiomeric ester thereof, which includes reacting an ester of (±) TBPA with a thermally stable and solvent-resistant esterase derived from *Bacillus brevis* 042-24.

In a preferable embodiment of the present invention, the ester of (±) TBPA is an ester selected from the group consisting of alkyl esters having 1 to 10 carbon atoms and alkoxyalkyl esters having 2 to 10 carbon atoms.

In a preferable embodiment of the present invention, the ester of (±) TBPA is an alkoxyalkyl ester having 2 to 10 carbon atoms.

The method of the present invention allows efficient production of an optically active TBPA having high optical purity and/or an enantiomeric ester thereof. Thus, the present invention provides an optically active intermediate for producing Compound (1), which is useful as an agent for treating hyperlipemia.

These and other advantages of the present invention will become apparent to those skilled in the art upon reading and understanding the following detailed description.

DESCRIPTION OF THE PREFERRED EMBODIMENT

Hereinafter, the present invention will be described more specifically.

The present invention is directed to a method for producing an optically active TBPA and/or an enantiomeric ester thereof by treating an ester of TBPA as a substrate with a hydrolytic enzyme derived from a microorganism. The reaction formula of the present invention is as follows.

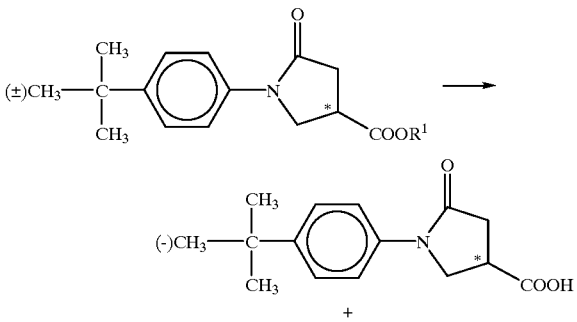

-continued

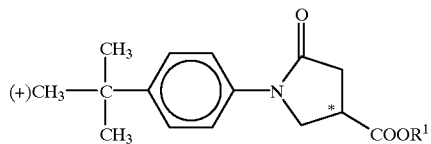

The ester of TBPA, which is the starting material of the present invention, can be selected in view of the substrate specificity of an enzyme used, the solubility in the reaction solvent, the ease of the separation after reaction, the availability of the alcohol as a raw material or the like.

Examples of the ester of TBPA include alkyl ester, alkoxyalkyl ester, alkenyl ester, haloalkyl ester, aryl ester and aryl alkyl ester. That is, in the above formula, an alkyl group, an alkoxyalkyl group, an alkenyl group, a haloalkyl group, an aryl group and an aryl alkyl group are preferably used as $R^1$.

As the alkyl group, an alkyl group having 1 to 10 carbon atoms, for example, methyl, ethyl, n-propyl, isopropyl, n-butyl, s-butyl, t-butyl, linear or branched pentyl, or linear or branched decyl group can be used. As the alkoxyalkyl group, the one having 2 to 10 carbon atoms, for example, methoxymethyl, methoxyethyl, ethoxyethyl or butoxyethyl group can be used. As the alkenyl group, for example, vinyl, allyl, isopropenyl or butenyl group can be used. As the haloalkyl group, for example, chlorethyl, chlorpropyl, bromoethyl, bromopropyl group can be used. As the aryl group and the arylalkyl group, for example, phenyl, benzyl, or phenethyl group where an alkyl, alkoxy, halogen, nitro, or acyl group may be introduced to the phenyl group can be used. Preferably, an alkyl group having 1 to 10 carbon atoms or an alkoxyalkyl group having 2 to 10 carbon atoms are used. Most preferable TBPA esters are alkoxyalkyl esters such as methoxyethyl ester.

The racemic isomer of TBPA (hereinafter referred to as racemic TBPA) and its ester can be synthesized easily by the method described in Japanese Laid-Open Patent Publication No. 3-275666. TBPA can be synthesized by reacting 4-t-butylaniline with itaconic acid under heating and melting. Then, the TBPA thus obtained is subjected to esterification to give an ester of TBPA easily. For example, the TBPA and alcohol are reacted in the presence of an acid catalyst such as a mineral acid or a Lewis acid so that an ester of the TBPA can be obtained. Alternatively, the racemic TBPA can be obtained by recemizing an optically active TBPA or its enantiomeric ester that is obtained as a result of the following enzyme reaction. The unnecessary optical isomer can be reused. Racemization can be effected, for example, by heating the optically active TBPA or its enantiomeric ester in water or a suitable organic solvent in the presence of a base.

As the enzyme derived from a microorganism used in the present invention, any one can be used, as long as it can hydrolyze an ester of the racemic TBPA in an optically selective manner so as to produce an optically active TBPA. An enzyme having high resistance to an organic solvent and high heat-stability can be preferably used. Examples of a preferable microorganism that produces the enzyme include the Bacillus brevis 042-24.

An ester-hydrolyzing enzyme (hereinafter referred to as esterase) can be obtained by culturing a microorganism which can produce esterase or a transformant to which an expression vector including a gene encoding an esterase is introduced, and purifying the cultured product.

The gene encoding the esterase can be isolated in the following manner, for example. First produced is a library to which a genomic DNA prepared from the esterase producing strain, Bacillus brevis 042-24, is inserted, Then, screening is performed with a probe that is prepared based on the amino acid sequence of part or the whole of the purified protein. Alternatively, screening is performed by using the expressed activity as the indicator, The expression of the esterase gene can be effected, for example, by inserting the isolated DNA fragment into a multi-copy vector or an expression vector including a strong promoter, then introducing such a vector to a suitable microorganism, and culturing the microorganism. As a host used for expression, any one can be used which is available for a DNA recombination technique. However, when a microorganism which also belongs to Gram-positive bacterium (e.g., Bacillus subtilis), the transformed strain is expected to efficiently secrete the esterase, as does Bacillus brevis 042-24.

Cultivation of the microorganism (including a transformant) can be performed by a known method. Preferably, a liquid culture medium can be used. The esterase can be purified from the cultured product in the following manner, for example. First, the cultured product is subjected to centrifugation or filtration so that a supernatant free from the microorganism can be obtained. Then, a fraction containing an esterase having heat-stability and solvent resistance can be obtained from the supernatant by conventional means such as concentration through ultra filtration or salting-out or solvent precipitation. This fraction is further subjected to precipitation, filtration, dialysis, or centrifugal separation, so that a crude enzyme can be obtained. Furthermore, this crude enzyme is subjected to a conventional method for an enzyme purification, such as lyophilization, isoelectric precipitation, electrophoresis, gel filtration chromatography, ion exchange chromatography and crystallization or a suitable combination of these methods, so that the crude enzyme or a purified enzyme having improved specific activity can be obtained.

Optically selective hydrolysis of the TBPA ester by the enzyme can be performed, for example, by dissolving the TBPA ester in a suitable solvent, adding a buffer solution and the enzyme thereto and stirring the mixture. The solvent used for the method of the present invention is not limited to a particular solvent, and any solvent can be used, as long as it does not inhibit the enzyme activity. Examples of the solvent include: aromatic hydrocarbons such as benzene, toluene and xylene; ketones such as acetone, methyl ethyl ketone and methyl isobutyl ketone; alcohols such as methanol, ethanol, isopropanol and n-butanol; esters such as ethyl acetate and butyl acetate; ethers such as diethyl ether; tetrahydrofuran and dioxane. Alternatively, water or a mixture of water and the above-mentioned organic solvent can be used. Preferable examples of solvents are: aromatic hydrocarbons such as benzene, toluene and xylene; and ketones such as acetone, methyl ethyl ketone and methyl isobutyl ketone.

In order to maintain an optimum pH for the enzymatic reaction, a buffer solution such as a phosphate buffer can be used together with the above-described organic solvent throughout all the processes of a conventional enzymatic reaction. The optimum pH is preferable about 4 to 9, more preferably about 6 to 8.

The amount of the enzyme used is not limited to a particular amount, but preferably is in the range of about 1 to 10 g/mol with respect to the TBPA ester as the substrate.

The reaction is conducted generally at about 10 to 70° C., preferably about 30 to 60° C., and more preferably about 40 to 50° C. The reaction time can be varied depending on the amount of the enzyme used, the reaction temperature, and pH of the reaction mixture. In general, the reaction is completed in about 4 to 24 hours.

Furthermore, the optimal end point of the reaction at which a reaction product with high optical purity is obtained can be determined by monitoring the progress of the reaction through an analysis method such as high performance liquid chromatography (hereinafter, referred to as HPLC).

The produced optically active TBPA and unreacted enantiomeric ester can be separated, for example, by conventional methods such as solvent extraction, column separation, and centrifugal separation, after the enzyme reaction is completed. For example, extraction with a solvent is performed in the following manner, for example. A suitable base is added to the reaction solution until the pH becomes about 7 to 9 and the TBPA is dissolved in an aqueous solution. Then, the unreacted enantiomeric ester is extracted with an organic solvent such as toluene, benzene, chloroform, ether, ethyl acetate, or methyl ethyl ketone. As the base, a hydroxide of an alkali metal such as NaOH and KOH or a carbonate or bicarbonate of an alkali metal such as $Na_2CO_3$, $K_2CO_3$ or $NaHCO_3$ can be used.

After the unreacted enantiomeric ester is extracted and separated, a mineral acid such as hydrochloric acid or sulfuric acid is added to the aqueous layer until the pH of the aqueous layer becomes acidic, and precipitated crystals are filtrated. Thus, the optically active TBPA can be obtained.

Optically active (−)-4-[1-(4-t-butylphenyl)-pyrrolidon-4-yl] methoxy benzoic acid [a compound where R is an hydrogen atom in the general formula (1)] can be produced easily by using the thus-obtained (−)-TBPA as a raw material according to the method described in Japanese Laid-Open Patent Publication No. 3-275666.

The enantiomeric ester thus-obtained can be saponified by a conventional method to give a TBPA enantiomer. The saponification can be performed, for example, by treating the ester (0.1M) with 1.1 equivalent of NaOH in an aqueous solution at room temperature for about 1 hour.

Optically active (+)-4-[1-(4-t-butylphenyl)-pyrrolidon-4-yl] methoxy benzoic acid can be produced easily according to the method described in Japanese Laid-Open Patent Publication No. 3-275666 and/or 6-192221 by employing the obtained TBPA enantiomer as a raw material.

EXAMPLES

Hereinafter, the present invention will be described more specifically by way of examples. A method for synthesizing a substrate, a method for preparing an enzyme solution, a method for a hydrolysis reaction, and a method for separating and recovering optical isomers will be described below. However, the present invention is not limited thereto.

Reference Example 1

Synthesis of a substrate, (±)-1-(4-t-butylphenyl)-5-oxo-3-pyrrolidine carboxylic acid methoxyethyl ester (hereinafter, referred to as (±)-TBP-MOE)

First, 200 g (0.77 mol) of (±)-TBPA, 640 mL of methoxy ethanol and 10 mL of concentrated sulfuric acid were introduced in a 2 L three-necked flask, and the reaction mixture was stirred at 80° C. for 12 hours. Then, 24 g of sodium carbonate was added thereto for neutralization, and the solvent was removed by distillation. Water was added to the residue, and extraction was performed with toluene. Thereafter, washing with 10% sodium carbonate followed by saturated sodium chloride solution was performed, and drying with anhydrous magnesium sulfate was performed. Thereafter, the solvent was removed by distillation. Thus, white crystals were obtained. Product: 207.7 g (yield: 85.0%), melting point: 60 to 61° C.

The characteristics of the reaction product were as follows:

<1>. Infrared absorption spectrum; KBr pellet method (hereinafter, referred to as IR (KBr)): ν: 2957, 1732, 1395, 1130, 837 $cm^{-1}$ <2>. Nuclear magnetic resonance spectrum; $^1$H-NMR at 400 MHz and $^{13}$C-NMR at 100 MHz (hereinafter, referred to as $^1$H-NMR and $^{13}$C-NMR respectively): $^1$H-NMR (CDCl$_3$), δ: 7.52 (d, 2H, J=8.4 Hz), 7.36 (9d, 2H, J=8.4 Hz), 4.20 (t, 2H), 4.00 (dm, 2H), 3.52 (t, 2H), 3.44 (m, 2H), 3.23 (s, 3H), 2.73 (dd, 2H), 1.25 (s, 9H) ppm <3>. Mass spectrum; gas chromatography mass-spectrometry (hereinafter, referred to as MS(El)): m/z; 312 (6%), 319(32%), 305(18%), 304(100%), 146(9%)

Reference Example 2

Isolation and Identification of the Microorganism

Soil samples collected in Hyogo prefecture were diluted with sterilized water, and were cultured on a LB agar plate containing 10 mg/ml of tributyline and 5 mg/ml of Noigen HC. A microorganism having esterase activity was isolated by selecting a clear zone formed in the periphery of the colony of the microorganism. The mycological properties of the obtained microorganism was investigated. The results were as follows.

A. Morphology
(1) Cell form: rod
(2) Cell size: 0.5×1.5 to 4.0 μm
(3) Mobility: +
(4) Spore: +(oval)
(5) Gram staining: +
(6) Acid-fast staining: −

B. Growth on Each Culture Medium
(1) Standard plate culture: translucent white, slightly flat, branched edge, smooth
(2) Standard slant culture: translucent white, smooth
(3) Standard liquid culture: turbid throughout the culture
(4) Standard gelatin-stab culture: turbid only in the upper portion
(5) Litmus milk: precipitation, peptonized in the upper portion C. Physiological Properties
(1) Reduction of nitrate: +
(2) Denitrification reaction: −
(3) Methyl red test: −
(4) Formation of acetyl methyl carbinol: −
(5) Formation of indole: −
(6) Formation of hydrogen sulfide: −
(7) Hydrolysis of starch: +
(8) Utilization of citrate: −
(9) Utilization of inorganic nitrogen source: nitrate: −, ammonium salt: −
(10) Formation of pigment: −
(11) Urease: −
(12) Oxidase: −
(13) Catalase: +
(14) Range of growth
  pH: 9.0 +, 5.7 −, 5.5 −, 5.0 −,
  Temperature: 10° C. −, 40° C. +, 45° C. −, 50° C. −
(15) Behavior toward oxygen: aerobic

(16) Formation of dihydroxyacetone: −
(17) Degradation of hippurate: −
(18) Degradation of amino acid: lysine −, arginine −, ornithine −
(19) Deamination of phenylalanine: −
(20) Temperature-resistance (85° C., 10 minutes): −
(21) Resistance to sodium chloride: 2.0% +, 5.0% −, 7.0% −, 10% −
(22) Growth with Sabouraud agar medium: −
(23) Growth with 0.001% lysozyme medium: −
(24) Degradation of tyrosine: +
(25) Alkali production with citric acid and ammonium agar: −
(26) Hydrolysis of casein: +
(27) Hydrolysis of gelatin: +
(28) Viability in anaerobic medium: −
(29) Growth with MacConkey's medium: −
(30) Lecithinase: −
(31) Alkali productivity in VP medium: −
(32) Utilization of saccharides and acid formation
  L-arabinose: −
  D-xylose: −
  D-glucose: +
  D-mannose: +
  D-Fructose: +
  D-Galactose:−
  Maltose: +
  Sucrose: +
  Lactose: −
  Trehalose +
  D-sorbitol: −
  D-mannitol: −
  Inositol: −
  Glycerol: +
  Starch: +
  Melibiose: −
  Salicin: +
  Ethanol: −
(33) Esculin hydrolysis: +
(34) Oxidation of gluconic acid: −

The above-described mycological properties were examined according to Bergey's Manual of Systematic Bacteriology, vol. 2, the 13th section. The results revealed that the microorganism was identified as a bacterium classified to the genus of Bacillus and the species of brevis, and was identified as *Bacillus brevis* 042-24. This strain was deposited on Feb. 20, 1997 in the National Institute of Bioscience and HumanTechnology Agency of Industrial Science and Technology, 1-1-1, Higashi, Tsukuba, Ibaraki, 305 Japan, under the deposition number of FERM BP-5827.

Reference Example 3

Preparation of Exogenous Enzyme

The *Bacillus brevis* 042-24 was inoculated in 1350 L of a medium (1.0% of soluble starch, 0.5% of polypeptone, 2.0% of yeast extract, and pH 7.0), and cultured under aeration and stirring at 28° C. for 24 hours (165 rpm and 1VVM). Thus, a culture broth was prepared. The culture supernatant was obtained by subjecting the culture broth to continuous centrifugation (20,000×g) so that the cells were removed. The obtained culture supernatant was concentrated to g105 L by ultrafiltration. Thereafter, 1.05 kg of lactose was added thereto, and vacuum drying was performed so that the enzyme powder was obtained in an amount of 2.9 kg. This was used as an enzyme preparation.

Example 1

Enzyme Reaction

In this example, an enzyme solution is prepared as follows: 1.5 g of the enzyme preparation obtained in Reference Example 3 was dissolved in 500 mL of a phosphate buffer (0.4 M and pH 7.5). Separately, a substrate solution was prepared as follows: 2 mL of toluene was added to 16 g of (±)-TBP-MOE and it was dissolved under heating. The substrate solution was added to the enzyme solution so as to prepare an enzyme reaction mixture. Then, a reaction was performed under stirring using a magnetic stirrer while the temperature was kept at 45° C. The reaction mixture was analyzed by HPLC and the reaction was stopped in 16 hours after the start of the reaction. The conditions under which the HPLC analysis was performed were as follows. Column: Opit-Pak TA (Waters Co. Ltd.), mobile phase: hexane/isopropanol/trifluoroacetic acid=(70/30/0.1), flow rate: 1 mL/min., and detection: UV, 245 nm.

The HPLC measurement provided the following results: the reaction ratio=54%, the optical purity of (−)-TBPA=85% e.e., and the optical purity of (+)-TBP-MOE=99% e.e.

Example 2

Separation and Recovery of Optical Isomers

After the reaction in Example 1 was completed, 5% sodium carbonate was added to the reaction mixture so that the reaction mixture became alkaline. Then, 250 mL of toluene was added to the mixture and then the mixture was separated. The solvent in the toluene layer was removed by distillation, and 7.2 g of (+)-TBP-MOE was obtained. The optical purity by HPLC was 99% e.e. The aqueous layer was washed with toluene two times, and then the pH of the aqueous layer was adjusted to 2 with sulfuric acid and crystals were precipitated and filtered off. Thus, 7.2 g of (−)-TBPA was obtained. The optical purity determined by HPLC was 85% e.e. The crystals were recrystallized from methanol, to give 5.9 g of purified (−)-TBPA. The optical purity determined by HPLC was 100% e.e.

Example 3

Evaluation of Optical Isomers

Identification data for the optical isomers were as follows.

<1>. IR (KBr), θ: 3000 to 5000 (br), 1725, 1625; 1508, 1414, 1278, 1208, 979 $cm^{-1}$.

<2>. $^1$H-NMR (DMSO-$d_6$), δ: 7.52(d, 2H, J=8.0Hz), 7.37 (d, 2H, J=8.0 Hz), 4.00 (m, 2H), 3.34 (m, 1H), 2.70 (m, 2H), 1.25 (s, 9H) ppm <3>. $^{13}$C-NMR (DMSO-$d_6$), δ: 174.7, 172.0, 147.0, 137.1, 125.8, 119.8, 50.4, 39.8, 35.7, 31.6 ppm <4>. Melting point: 230° C. to 231° C.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for producing an optically active 1-(4-t-butylphenyl)-5-oxo-3-pyrrolidine carboxylic acid and/or an enantiomeric ester thereof comprising treating an ester of (±)-1-(4-t-butylphenyl)-5-oxo-3-pyrrolidine carboxylic acid with an esterase derived from *Bacillus brevis* 042-24 FERM BP-5827.

2. The method according to claim 1, wherein the ester of (±)-1-(4-t-butylphenyl)-5oxo-3-pyrrolidine carboxylic acid is an ester selected from the group consisting of alkyl esters having 1 to 10 carbon atoms and alkoxyalkyl esters having 2 to 10 carbon atoms.

3. The method according to claim 1, wherein the ester of (±)-1-(4-t-butylphenyl)-5-oxo-3-pyrrolidine carboxylic acid is an alkoxyalkyl ester having 2 to 10 carbon atoms.

4. The method according to claim 1, wherein the treatment is conducted at a temperature from about 40 to 50° C.

5. The method according to claim 4, wherein the temperature is about 45° C.

* * * * *